US005520634A

United States Patent [19]
Fox et al.

[11] Patent Number: 5,520,634
[45] Date of Patent: May 28, 1996

[54] MECHANICAL MORCELLATOR

[75] Inventors: William D. Fox, New Richmond; Harry C. Parkhurst, Cincinnati, both of Ohio

[73] Assignee: Ethicon, Inc., Somerville, N.J.

[21] Appl. No.: 274,112

[22] Filed: Jul. 12, 1994

Related U.S. Application Data

[63] Continuation of Ser. No. 52,255, Apr. 23, 1993, abandoned.

[51] Int. Cl.⁶ ..................... A61B 17/32
[52] U.S. Cl. ............ 604/22; 606/170; 606/180
[58] Field of Search .................. 606/180, 170, 606/171, 159, 80; 604/22; 408/710; 83/DIG. 1

[56] References Cited

U.S. PATENT DOCUMENTS

| | | | |
|---|---|---|---|
| 2,710,000 | 6/1955 | Cromer et al. | 606/180 X |
| 3,120,845 | 2/1964 | Horner | 606/180 |
| 3,614,953 | 10/1971 | Moss | 606/170 X |
| 3,780,246 | 12/1973 | Beckering et al. | 200/157 |
| 4,381,037 | 4/1983 | Cuneo | 408/710 X |
| 4,461,305 | 7/1984 | Cibley | 606/180 X |
| 4,790,812 | 12/1988 | Hawkins et al. | 604/22 |
| 4,792,327 | 12/1988 | Swartz | 606/170 X |
| 5,030,201 | 7/1991 | Palestrant | 604/22 |
| 5,123,904 | 6/1992 | Shimomura et al. | 606/170 X |
| 5,133,713 | 7/1992 | Huang et al. | 606/180 X |
| 5,135,531 | 8/1992 | Shiber | 606/180 X |

FOREIGN PATENT DOCUMENTS 4038398  6/1992  Germany ............... 606/180

OTHER PUBLICATIONS

Surgical Laparoscopy & Endoscopy, Laparoscopic Nephrectomy: A Review of 16 Cases, Ralph V. Clayman et al., vol. 2, No. 1, pp. 29–34.

*Primary Examiner*—Michael H. Thaler
*Attorney, Agent, or Firm*—Paul A. Coletti

[57] ABSTRACT

The present invention is directed towards a mechanical morcellator which includes a rotatable and relatively retractable cutting head. User manipulation varies the amount the cutting head extends out of a sheath, the amount of suction communicated to the cutting head, and the operation of a motor which rotatably drives the cutting head. Suction is communicated to the cutting head to aspirate the tissue fragmented by the cutting head. The morcellator is adapted to be inserted through a laparoscopic port site and directly fragment and aspirate tissue from within a patient's body. Alternate embodiments of the present invention provide different cutting head extension and retraction devices. The morcellator of the present invention allows removal of tissue without the need for large entry incisions.

11 Claims, 4 Drawing Sheets

MECHANICAL MORCELLATOR

This is a continuation of application Ser. No. 08/052,255, filed Apr. 23, 1993 now abandoned.

BACKGROUND OF THE INVENTION

1. Field of the Invention

The present invention is generally directed to tissue removal devices and, more particularly, to mechanical morcellation devices.

2. Description of the Related Art

During surgical procedures and, more particularly, tissue removal procedures, it is desirable to limit the size of the entry incision to minimize the trauma experienced by the patient. In the past, efforts to minimize entry incision size have generally been limited due to the size of the tissue to be removed and the need for access to the tissue.

However, in modern surgery access to the organ is provided by inserting one or more trocar and cannula to the tissue cite. Thereafter, one or more laparoscopes are used to view the tissue to be removed, and additional port sites are used to gain access to the tissue to sever it from tissue which is to remain. However, the entry incision must still be sized to allow removal of the severed tissue and, therefore, the reduction in entry incision size is rather limited even in more modern or recently developed surgical procedures.

One system which has been developed to overcome this limitation is described in *Laparoscopic Nephrectomy: A review of 16 Cases,* Surgical Laparoscopy & Endoscopy, Vol. 2, No. 1, pp. 29–34 (Raven Press, Ltd., 1992), the disclosure of which is expressly incorporated herein in its entirety. This publication describes a method for removing renal tissue using a mechanical morcellator. In this method of removal, the kidney and associated renal tissue, after being severed from the ureter, renal arteries, and veins, are placed in an impermeable containment bag. The neck of the bag is closed, withdrawn from a laparoscopic port site, and reopened to gain access to the tissue contained therein. Thereafter, with the tissue remaining in the bag within the patient's body, a morcellator cutting head is introduced into the bag and activated, fragmenting and aspirating the renal tissue. The aspirated tissue is retained within a filtering chamber within the morcellator handle, which must be cleaned following the surgical procedure.

Although the morcellation device and method disclosed in this reference represents an improvement over tissue removal methods which require a large entry incision, several undesirable structural and operational features remain.

The morcellation techniques known in the art do not provide a cover for the cutting head or allow relative extension and retraction of the cutting head. Also, the known morcellators do not provide means, whether electrical or mechanical, to prevent the accidental or unintentional actuation of the morcellator cutting head. Moreover, the known morcellators are not ergonomically designed, and are rather bulky and cumbersome in use. These undesirable features cooperate to create a mechanical morcellator which is susceptible to accidental or unintentional actuation.

Therefore, there exists a need in the art for an effective mechanical morcellator which provides a relatively movable cutting head and which includes means to prevent the unintentional actuation of the morcellator cutting head. There also exists a need for a mechanical morcellator which aspirates fragmented tissue to an exterior retention means and for a morcellator satisfying the deficiencies in the prior art which is ergonomically designed to make handling and use thereof more convenient for the surgeon.

SUMMARY OF THE INVENTION

In accordance with the present invention there is provided a mechanical morcellator which is operable to fragment and aspirate tissue. The mechanical morcellator includes a rotary cutting head which communicates with suction via a hollow drive tube. The cutting head is driven by a variable speed electric motor via the drive tube, the speed of the motor being preset by a user-manipulated control box.

The mechanical morcellator includes a cutting head extension means. The cutting head extension means includes a sheath which extends between the morcellator body and the cutting head. The sheath covers the cutting head when in a first position and reveals the cutting head when in a second position. Means are provided to allow user manipulation or adjustment of the sheath position relative to the cutting head.

In further accordance with the present invention, means are provided to prevent the unintentional or accidental actuation of the cutting head. The mechanical morcellator also includes suction control means. The suction control means includes a valve which is integral with the trigger and coordinated with the cutting head operation to limit suction flow to the cutting head when the cutting head is inoperable, while permitting full suction flow thereto when the head is operating.

The mechanical morcellator of the present invention provides the various functional and structural features in an ergonomically designed "pistol grip" handle which facilitates the surgeon's operation and manipulation of the morcellator.

BRIEF DESCRIPTION OF THE DRAWINGS

These and additional features of the present invention will be apparent with reference to the following description and drawing figures, wherein.

DETAILED DESCRIPTION OF THE PREFERRED EMBODIMENT

Figure 1:
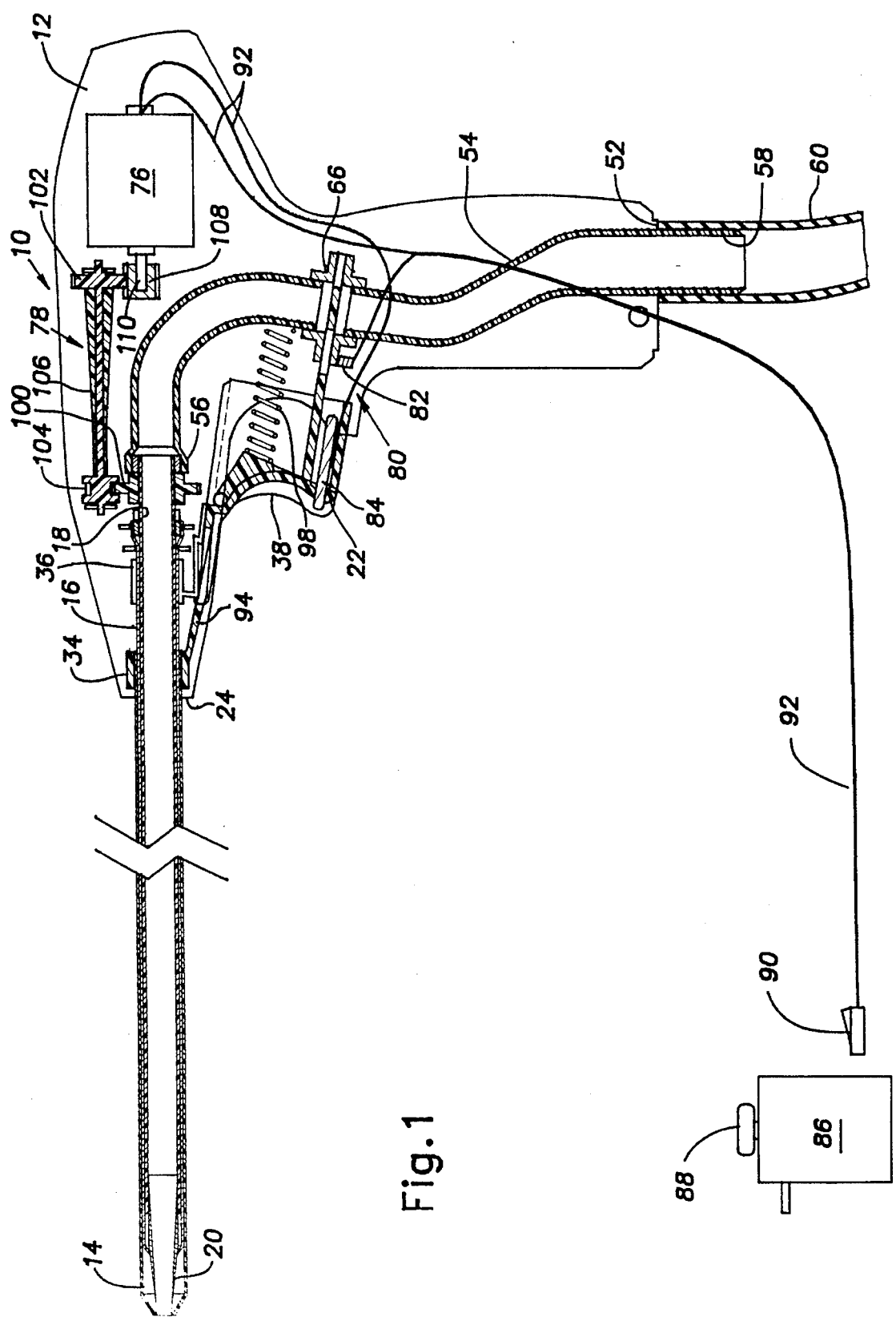
FIG. 1 is an elevational view, in cross section, of a first embodiment of the mechanical morcellator of the present invention.

With reference to the drawing figures, the mechanical morcellator 10 of the present invention is shown to generally include a handle 12, a sheath 14, a barrel 16, a drive tube 18, a rotary cutting head 20, and a trigger 22.

The handle 12, which is preferably formed in two mating halves of polycarbonate or ABS plastic, provides a front aperture 24 through which the sheath 14, barrel 16, and drive tube 18 extend. At the front aperture 24 the drive tube 18 is rotatably received within the barrel 16, which is slidably received within the sheath 14. As illustrated, the sheath 14, barrel 16, and drive tube 18 are coaxial and generally tubular in shape.

Preferably, the barrel 16 is stainless steel, having an outside diameter of about 0.375 inches and a wall thickness of about 0.016 inches, the drive tube 18 is plastic, having an inside diameter of about 0.300 inches and an outside diameter of about 0.330 inches, and the sheath 14 is TEFLON or ethylene having an outside diameter of about 0.410 inches and a wall thickness of about 0.010 inches.

The barrel 16 surrounds the drive tube 18 and extends outwardly therewith from the handle 12 to the cutting head 20. The barrel 16 is rigidly mounted to the handle to prevent the barrel from rotating with the drive tube 18, and includes an outwardly flared proximal end 26 into which is press fit a first rear sleeve bearing 28. There is a gap of about 0.045 inches between the barrel 16 and the drive tube 18, allowing the drive tube to rotate without frictional interference with the barrel.

The barrel 16 is surrounded by the sheath 14 which extends outwardly therewith towards the cutting head 20. The sheath 14 has a proximal end 30 (FIG. 2) and a tapered distal end 32 (FIG. 3). The distal end 32 of the sheath 14 generally surrounds the cutting head 20 while the sheath is in the outward or "at rest" position. The proximal end 30 of the sheath 14 is press fit into a cylindrical sheath receptacle 34 provided by the trigger 22, as illustrated.

Preferably, a sheath stop 36 is rearwardly spaced from the sheath receptacle 34 to limit rearward longitudinal movement of the sheath 14 to about 0.435 inches. The sheath stop 36, which is secured to the handle 12 and slip-fit over the barrel 16, provides first and second latching surfaces A and B which are releasably engaged by a trigger latch 38 associated with the trigger 22, as will be described hereafter. Preferably, the latching surfaces A and B are about 0.400 inches apart.

As illustrated in FIG. 3, the cutting head 20 is generally frustoconical in shape, having a proximal section 40 which is generally larger than a distal section 42. Preferably, the proximal section 40 of the cutting head 20 has an outside diameter of about 0.300 inches to generally match the inside diameter of the drive tube 18, and thereby allow the proximal section 40 of the cutting head 20 to be press fit into a distal end 44 of the drive tube 18 (FIG. 3). The distal section 42 of the cutting head 20, which includes a razor-sharp tip 46, preferably has a diameter of about 0.200 inches.

A distal end 48 of the barrel 16 extends past the distal end 44 of the drive tube 18 and has press fit therein a front sleeve bearing 50. The front sleeve bearing 50, which is preferably made of TEFLON FEP, slidably fits over the cutting head 20 and is press fit into the barrel 16. The proximal section 40 of the cutting head 20 is press fit into the distal end 44 of the drive tube 18, and slidably and rotatably received by the front sleeve bearing 50.

The sheath 14 extends past the distal end 48 of the barrel 16, generally covering the distal section 42 of the cutting head 20. The tapered distal end 32 of the sheath 14, which provides an opening of about 0.280 inches through which the cutting head extends, is generally coterminous with the cutting head 20 when the trigger 22 is in the at-rest position. When the trigger is moved inwardly or rearwardly (i.e. to the right in FIGS. 1 and 2) the cutting head 20 telescopingly extends out of the distal end 32 of the sheath 14, allowing the razor-sharp tip 46 of the cutting head 20 to engage and fragment tissue.

The handle 12 also provides a downwardly directed opening 52 through which a rigid suction tube 54 extends.

The suction tube 54, which is rigidly attached to the handle 12, includes inner and outer ends 56 and 58. The outer end 58 of the suction tube 54 is received by an external flexible vacuum hose 60 (FIG. 1) while the inner end 56, which is radially-outwardly flared, receives a proximal end 62 of the drive tube 18. The external flexible vacuum hose 60 connects to an external suction source (not shown) and a tissue collection means (not shown). Preferably, the rigid suction tube 54 has an inside diameter of about 0.300 inches and a gentle curvature, as illustrated, to provide unrestricted vacuum flow therethrough.

Midway along its length the suction tube 54 is separated to allow mounting of a suction control valve 64 therein. A cylindrical mounting plate 66 interconnects the separated portions of the suction tube 54 and includes a radially-outwardly projecting or annular surface 68 which defines a slot 70 through which the suction control valve 64 extends, as illustrated.

The suction control valve 64, which is integral with the trigger 22, defines an opening 72 which extends into the lumen defined by the suction tube 54 when the trigger 22 is inwardly-moved, as will be described more fully hereafter. Preferably, the opening 72 is sized and positioned such that, when the trigger 22 is in the fully-retracted position, the opening 72 coincides with the lumen provided by the suction tube 54, thereby allowing maximum suction to be communicated to the cutting head 20.

The flared inner end 56 of the rigid suction tube 54 has press-fit therein a second rear sleeve bearing 74 which, in turn, is press fit onto the proximal end 62 of the drive tube 18. The cutting head 20, drive tube 18, rigid suction tube 54 and flexible vacuum hose 60 comprise a suction flow path which allows communication of fragmented tissue from the rotary cutting head 20 to the external suction source and tissue collector.

A variable speed drive means is provided to rotatably drive the drive tube 18 and, hence, the cutting head 20. The drive means includes a motor 76, transmission 78, a switch 80, and the trigger 22. The switch 80 comprises a first bronze contact 82 pressed into the handle 12 adjacent the cylindrical mounting plate 66 and a second bronze contact 84 associated with the trigger 22.

When the trigger 22 is in an at-rest or initial position (FIG. 1), the switch 80 (i.e. the first and second contacts 82 and 84) represent an open circuit. Thus, no current is supplied to the motor 76, and the drive tube 18 and cutting head 20 are stationary. The motor 76 is electrically connected to power via the switch 80 and a transformer or control box 86 when the trigger 22 is in the inwardmost or full-retracted position, as will be described more fully hereafter.

The control box 86 includes a rotary pot 88 to allow a user to preset the maximum power available to the morcellator 10 and, hence, the maximum speed of the cutting head 20. Electrical connectors 90 and appropriate lengths of electrical conductors 92 are between the control box 86 and the switch 80 and motor 76. Preferably, the conductors 90 are four-wire cables and the connectors 92 are four-pin connectors.

The trigger 22 nests within a track provided by the handle 12, and is manually movable by the surgeon, total range of travel being generally equal to the sheath travel (i.e. about 0.435 inches). The trigger 22, which is preferably formed out of plastic, includes the metal trigger latch 38 which slidably extends out of a slot in the trigger 22. The trigger 22 also includes an outwardly extending portion 94 which terminates in the cylindrical sheath receptacle 34.

The outwardly extending portion 94 defines an opening through which a hooked terminal end 96 of the trigger latch 38 extends. The hooked terminal end 96 of the trigger latch 38 is operable to releasably engage the first and second latching surfaces A and B.

The trigger latch 38, which is resiliently biased to extend through the trigger 22, pivots about pivot point C. The second contact 84, which is slidably received by the trigger 22, is press fit into the trigger latch 38 and moves therewith. When the trigger 22 and trigger latch 38 are in the at-rest position shown in FIGS. 1 and 2, the hooked terminal end 96 is in engagement with the first latching surface A, there is a gap of about 0.075 inches between the trigger latch 38 and the trigger 22 at point D on FIG. 2, and the first and second contacts 82 and 84 are separated by approximately 0.496 inches. When the trigger 22 and trigger latch 38 are in the inwardmost or rearwardmost position, the trigger and trigger latch are generally in contact at point D, and the first and second contacts 82 and 84 are in engagement.

A trigger return spring 98, which is mounted between the trigger 22 and a portion of the handle, biases the trigger 22 and the trigger latch 38 to the at-rest or outward position. Preferably, the trigger return spring 98 has an inside diameter of about 0.200 inches and about three pounds maximum spring force.

The transmission 78, which transfers rotational motion from the motor 76 to the drive tube 18, includes a spur gear 100, a driven gear 102, and a drive gear 104. The spur gear 100, which is press fit onto the drive tube 18 intermediate the first and second rear sleeve bearings 28 and 74, meshes with the drive gear 104. The drive gear 104 is connected to the driven gear 102 via a transmission shaft 106. The driven gear 102 meshes with a pinion gear 108 which is press fit onto a motor output shaft 110. As will be recognized by one skilled in the art, the rotational motion of the motor output shaft 110 is transferred to the driven gear 102 via the pinion gear 108, and thereafter communicated to the spur gear 100 and drive tube 18 via the transmission shaft 106 and drive gear 104.

The mechanical morcellator 10 of the present invention operates in the following manner. After the tissue to be removed is severed from the tissue to remain, the morcellator 10 is inserted via an existing laparoscope port site to the location of the tissue. Optionally, the severed tissue is confined within an impermeable bag (not shown), preferably of nylon or the like, to prevent the migration of tissue during morcellation thereof. In the preferred embodiment the sheath 14, barrel 16, and drive tube 18 extend approximately ten inches from the handle 12, allowing the cutting head 20 to reach the tissue within the patient's body. The morcellator is not in operation during insertion and the electrical and mechanical means described previously prevent the unintentional operation thereof.

If the tissue to be removed is to be fragmented and aspirated without being preliminarily captured in an impermeable bag, the surgeon views the tissue to be removed and the distal ends 32 and 44 of the sheath 14 and cutting head 20 via a laparascope (not shown). Otherwise, the tissue is preliminarily captured within an impermeable bag, the mouth of the bag is withdrawn from one of the laparoscopic ports, and the distal ends 32 and 44 of the sheath 14 and the cutting head 20 are inserted into the bag via the open mouth.

In either case, the trigger 22 and trigger latch 38 are rearwardly or inwardly moved against the bias of the trigger return spring 98. Rearward or inward force on the trigger latch 38 initially causes the trigger latch 38 to pivot about pivot point C and disengage the hooked terminal end 96 of the trigger latch 38 from the first latching surface A. Thereafter, the trigger 22 and trigger latch 38 are free to move rearwardly against the bias of the trigger return spring 98 until the cylindrical sheath receptacle 34 engages the sheath stop 36. Rearward movement of the trigger 22 and associated sheath receptacle 34 simultaneously moves the sheath 14 rearwardly, exposing the distal section 42 of the cutting head 20 and the razor sharp tip 46 provided thereby.

As the trigger 22 moves rearwardly, the suction control valve 64 provided thereby and, more specifically, the opening 72 in the suction control valve 64, extends into the lumen defined by the suction tube 54. The further the trigger 22 is depressed, the more the opening 72 extends into the lumen of the suction tube 54, thus communicating suction to the cutting head 20 in proportion to the amount the cutting head extends out of the sheath 14.

During movement of the trigger 22 and exposure of the cutting head 20, the first and second contacts 82 and 84 are spaced from each other and, hence, the motor 76 is not connected to power and does not rotatably drive the cutting head 20 via the drive tube 18. When the trigger approaches its inwardmost position, the combination of trigger 22 and trigger latch 38 movement allows the first and second contacts 82 and 84 to engage and connect the motor 76 to power, the level of which was preset by user manipulation of the control box 86. Rotational motion of the motor output shaft 110 is transferred through the transmission 78 and drive tube 18 to the cutting head 20.

The surgeon moves the razor sharp tip 46 of the cutting head 20 into engagement with the tissue to be removed, fragmenting the tissue. The fragmented tissue, typically in the form of a cylindrical or rod-like core of tissue, is thereafter aspirated into the external tissue collection means via the drive tube 18, suction tube 54, and vacuum hose 60. The core of tissue may simplify and expedite examination and study of the severed tissue as compared to the ground-up tissue which results from prior art morcellators.

When the procedure is complete, the surgeon merely releases the trigger 22 which opens the switch 80, turns off the motor 76, precludes communication of suction to the cutting head 20, and returns the sheath 14 to its at-rest position covering the cutting head 20.

If, while the trigger 22 is being rearwardly moved between the first and second latching surfaces A and B, the trigger latch 38 is released, the trigger return spring 98 will cause the trigger latch 38 to pivot about pivot point C and thereby return the trigger latch 38 to its at-rest or outward position. Further rearward movement of the trigger 22 will cause the hooked terminal end 96 to engage the second latch surface B, preventing further rearward movement of the trigger 22 and sheath 14 until the trigger latch 38 is depressed by the user. Also, if the trigger 22 and trigger latch 38 are released between the first and second latching surfaces A and B, and the sheath 14 is rearwardly pushed, perhaps due to frictional contact with tissue surrounding the sheath 14, the second latching surface B will be engaged by the hooked terminal end 96 of the trigger latch 38 and prevent the further rearward movement of the sheath 14 until the trigger latch 38 is rearwardly-moved against the bias of the trigger return spring 98.

As should be clear from the foregoing, the combination of the relatively moveable sheath 14, the trigger latch 38, and the switch 80 cooperate to provide a mechanical morcellator which prevents the accidental or unintentional actuation or operation thereof. Specifically, there is a range of motion to the trigger 22 and trigger latch 38 which is necessary in order to actuate the motor 76. Moreover, accidental actuation of the razor sharp tip 46 of the cutting head 20 is not possible without first rearwardly moving the trigger 22 and trigger latch 38. Therefore, the risk of accidental or unintentional actuation of the razor sharp tip 46 is significantly reduced as compared to known mechanical morcellators.

Figure 2:
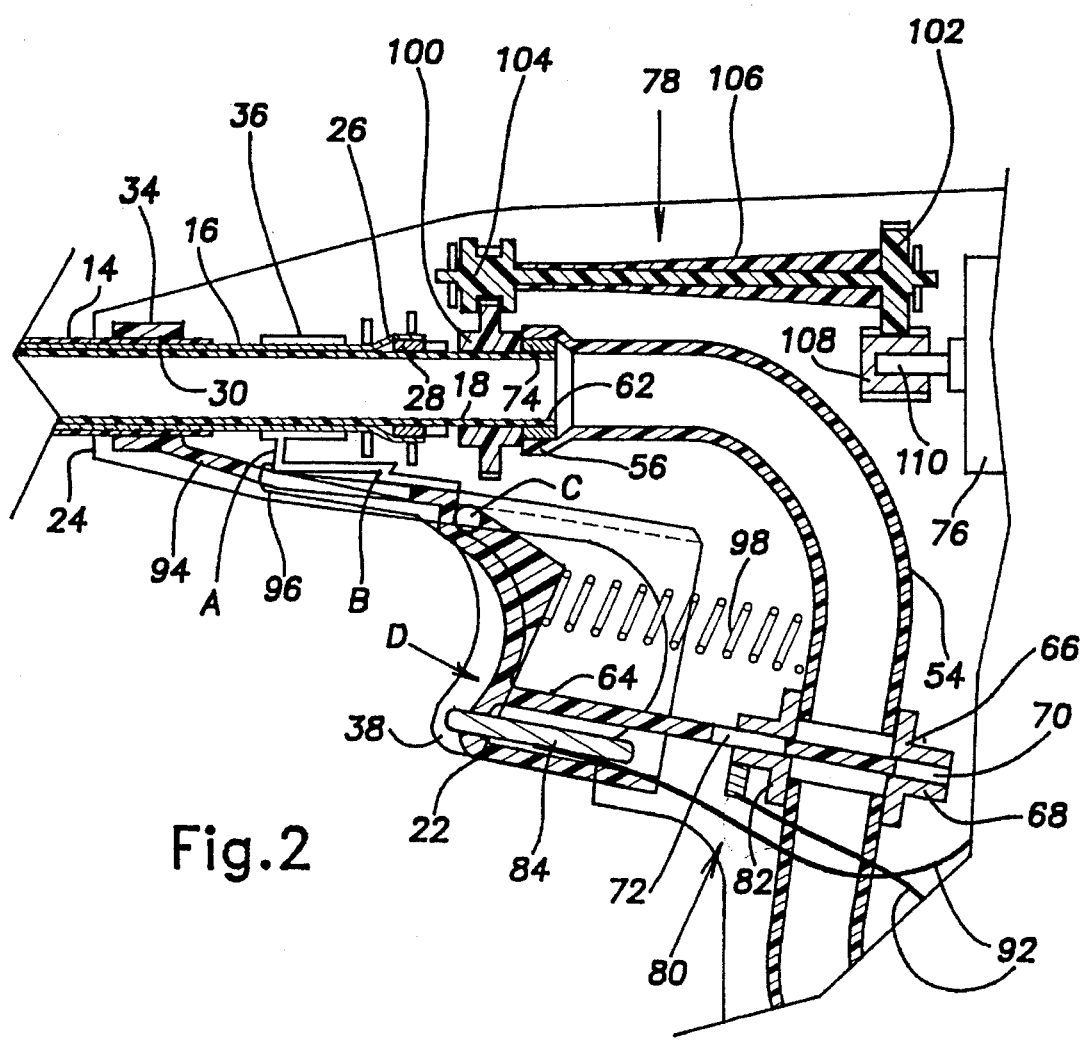
FIG. 2 is an enlarged elevational view, in cross section, of the handle of the embodiment shown in FIG. 1.
Figure 3:
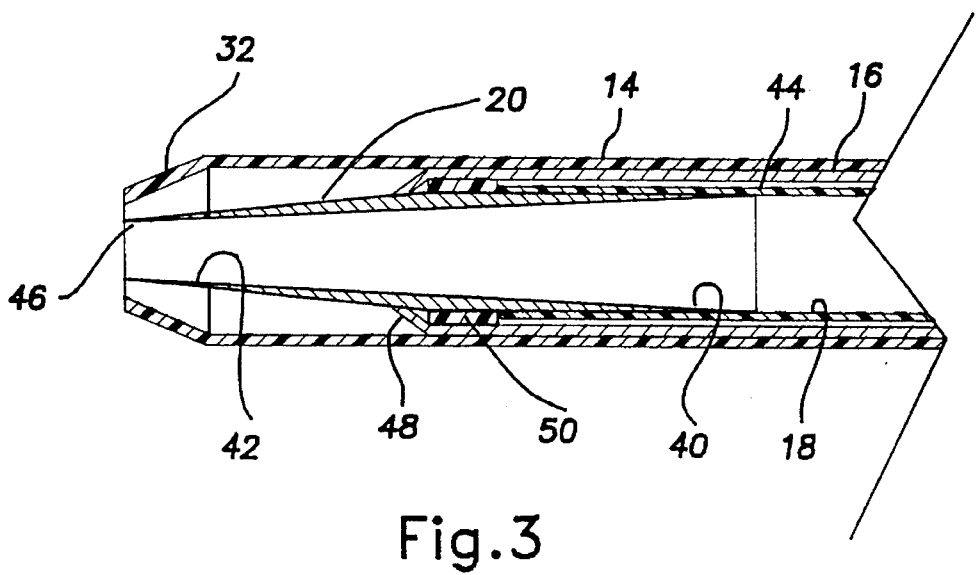
FIG. 3 is an enlarged elevational view, in cross section, of the cutting head.
Figure 4:
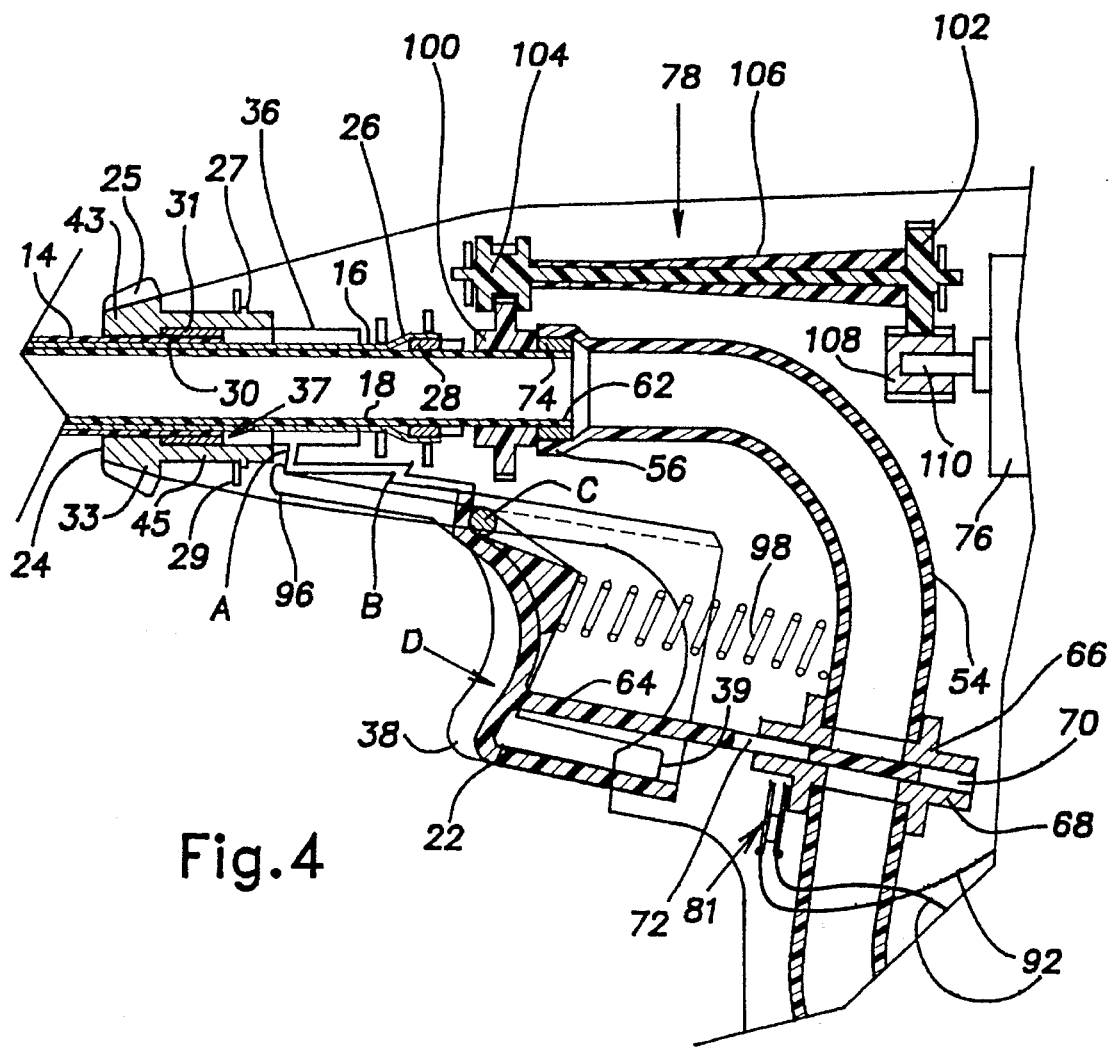
FIG. 4 is an enlarged elevational view, in cross section, of the handle of a second embodiment of the present invention; and, FIG. 5. is an enlarged elevational view, in cross section, of the handle of a third embodiment of the present invention.
Figure 5:
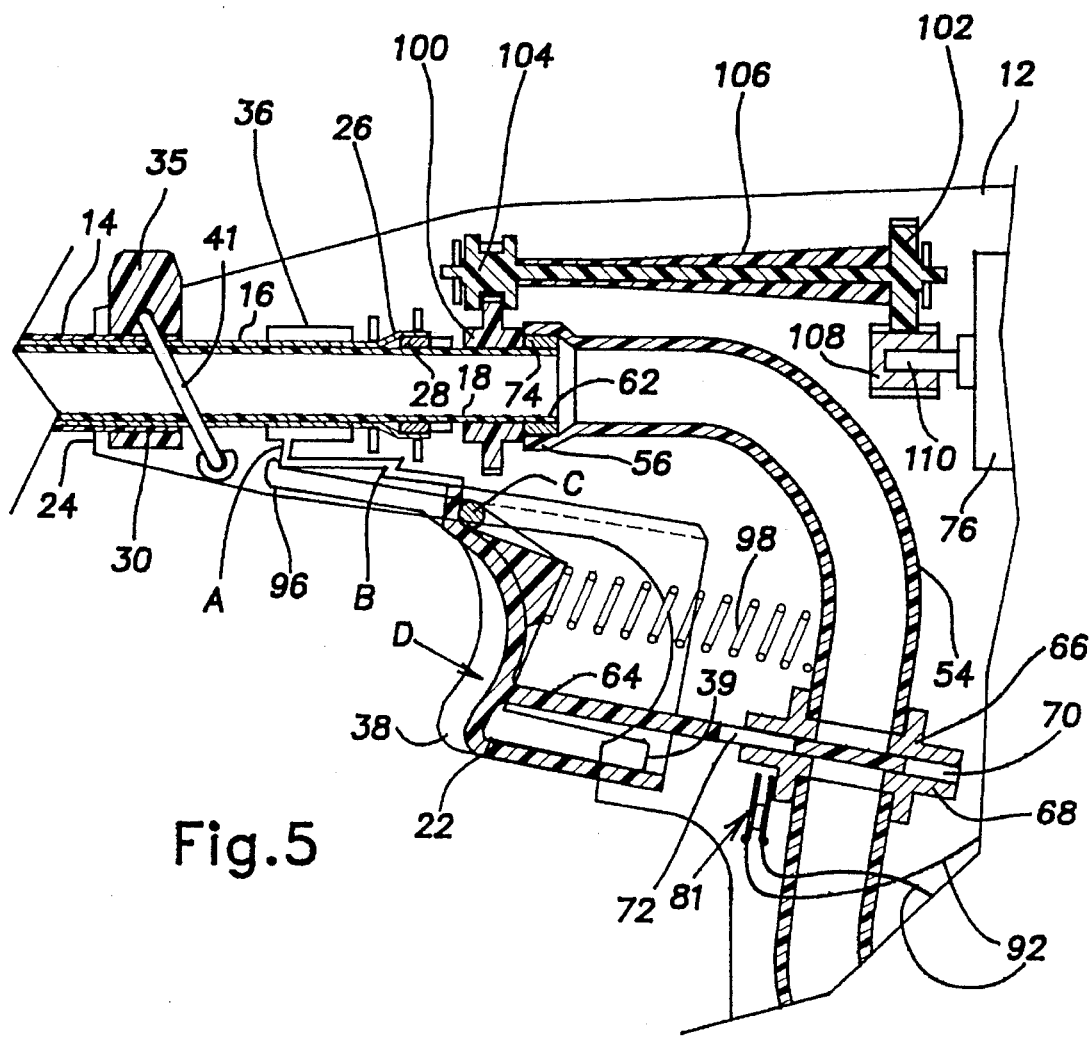

Second and third embodiments of the present invention are illustrated in FIGS. 4 and 5, respectively, wherein, when possible, the reference numerals used to describe the first embodiment illustrated in FIGS. 1–2 have been employed. As will be apparent with reference to the drawing figures, several structural features of the first embodiment are present in the second and third embodiments, and will not be further described herein. Also, the details of the cutting head shown in FIG. 3 are unchanged in the second and third embodiments, and, therefore, will not be further described herein.

The morcellator shown in FIG. 4 includes the handle 12, sheath 14, barrel 16, drive tube 18, cutting head 20 (FIG. 3), and trigger 22. The handle 12, which is preferably formed in two mating halves of polycarbonate or ABS plastic, provides a front aperture 24 through which the sheath 14, barrel 16, and drive tube 18 extend. Surrounding the front aperture 24, the handle 12 provides an enlarged nose portion 25 which provides a cylindrical cavity projecting rearwardly from the front aperture 24.

The sheath 14 has a proximal end 30 and a tapered distal end 32 (FIG. 3). The proximal end 30 of the sheath 14 is press fit into an exteriorly threaded bushing 31 which, in turn, is threaded into an annular or ring-shaped rotary sheath knob 33. The sheath 14, barrel 16, and drive tube 18 extend through a central opening provided by the sheath knob 33. The rotary sheath knob 33 includes a relatively thick cylindrical portion 43, which is received by the cylindrical cavity defined by the enlarged nose portion 25, and a thinner elongated cylindrical portion 45, which extends inwardly from the thick cylindrical portion 43 towards a sheath stop 36, as illustrated. The elongated cylindrical portion 45 includes an annular rim 27 which engages a stop 29 to help retain the sheath knob 33 within the handle 12.

The sheath knob 33 and, more particularly, the thick cylindrical portion 43, is accessible to the user for manipulation via one or more openings (not shown) in the handle 12. As mounted within the handle 12, the sheath knob 33, which is only capable of rotary movement, threadably engages the bushing 31 and compels the bushing 31 and, hence, the sheath 14, which is press-fit therein, to move longitudinally or lengthwise. Thus, rotary movement of the sheath knob 33 is translated into longitudinal movement of the sheath 14, thereby allowing the user to vary the amount the cutting head 20 extends out of the sheath 14.

Preferably, the sheath stop 36 is rearwardly or inwardly spaced from a terminal end 37 of the sheath 14 and threaded bushing 31 to limit rearward longitudinal movement of the sheath 14 to about 0.435 inches. The sheath stop 36, which is secured to the handle 12 and slip-fit over the barrel 16, also provides first and second latching surfaces A and B which are releasably engaged by a trigger latch 38 associated with the trigger 22. Preferably, the latching surfaces A and B are about 0.400 inches apart.

A variable speed drive means is provided to rotatably drive the drive tube 18 and, hence, the cutting head 20. The drive means includes the motor 76, transmission 78, switch 81, and the trigger 22. The switch 81 is mounted to the handle 12 adjacent the cylindrical mounting plate 84 and is actuated when the trigger 22 is moved to its inwardmost or rearwardmost position, as will be described hereafter.

The trigger 22 nests within a track provided by the handle 12, and is manually movable by the surgeon, total range of travel being about 0.445 inches. The trigger 22 is preferably made out of plastic and includes a metal trigger latch 38 which slidably extends out of a slot in the trigger 22. The trigger latch 38 pivots about pivot point C and includes a hooked terminal end 96 which is operable to releasably engage the first and second latching surfaces A and B. The trigger latch 38 also includes an inwardly directed portion 39 which is operable to actuate the switch 81, as will be described more fully hereafter.

When the trigger 22 and trigger latch 38 are in the at-rest position shown in FIG. 4, the hooked terminal end 96 is in engagement with the first latching surface A, and there is a gap of about 0.075 inches between the trigger latch 38 and the trigger 22 at point D on FIG. 4. A trigger return spring 98, which is mounted between the trigger 22 and a portion of the handle 12, biases the trigger 22 and the trigger latch 38 to the at-rest or outward position. When the trigger 22 and trigger latch 38 are in the inwardmost or rearwardmost position, the inwardly directed portion 39 is in engagement with the switch 81, and the trigger and trigger latch are generally in contact at point D.

The mechanical morcellator 10 of the second embodiment operates in the following manner. Following severance of the tissue to be removed from the tissue to remain, the morcellator 10 is inserted via an existing laparoscope port. Optionally, and as discussed with reference to the operation of the first embodiment of the present invention, the severed tissue is confined or placed within an impermeable bag, preferably of nylon or the like, to prevent the migration of tissue during morcellation thereof. In the preferred embodiment the sheath 14, barrel 16, and drive tube 18 extend approximately 9.70 inches from the handle 12, allowing the cutting head 20 to reach the tissue within the patient's body. The morcellator 10 is not in operation during insertion and the electrical and mechanical means described previously prevent the unintentional operation thereof.

While the surgeon views the tissue to be removed and the distal ends 32 and 44 of the sheath 14 and cutting head 20, the rotary sheath knob 33 is manipulated or rotated by the surgeon, causing the bushing 31 and sheath 14 to move rearwardly (i.e., to the right as viewed in FIG. 4) and expose the cutting head 20. The surgeon discontinues his adjustment or manipulation of the rotary sheath knob 33 when the cutting head 20 extends out of the sheath 14 the desired amount.

Thereafter, the trigger 22 and trigger latch 38 are rearwardly or inwardly moved against the bias of the trigger return spring 98. Rearward force on the trigger 22 and trigger latch 38 initially causes the trigger latch 38 to pivot about pivot point C and disengage the hooked terminal end 96 from the first latching surface A. Thereafter, the trigger 22 and trigger latch 38 are free to move rearwardly against the bias of the trigger return spring 98. Naturally, if the trigger latch 38 is released while the trigger 22 is being rearwardly moved between the first and second latching surfaces A and B, the trigger return spring 98 will cause the trigger latch to pivot about the pivot point C and, thus, return the trigger latch 38 to its at-rest or outward position. This, in turn, will cause the hooked terminal end 96 of the trigger latch 38 to engage the second latch surface B, and thereby prevent further rearward movement of the trigger 22 until the trigger latch 38 is depressed by the user.

As the trigger 22 moves rearwardly, the suction control valve 64 provided thereby and, more specifically, the opening 72 in the suction control valve 64, extends into the lumen defined by the suction tube 54. The further the trigger 22 is rearwardly moved, the more the opening 72 extends into the lumen, thus communicating relatively more suction to the cutting head 20.

During movement of the trigger 22 and exposure of the cutting head 20, the switch 81 is open and, hence, the motor 76 is not connected to power and does not rotatably drive the cutting head 20. When the trigger 22 approaches its inwardmost or rearwardmost position, the combination of trigger 22 and trigger latch 38 movement allows the inwardly directed portion 39 of the trigger latch 38 to contact and actuate the switch 81 and thereby connect the motor 76 to power. Rotational motion of the motor output shaft 110 is transferred through the transmission 78 and drive tube 18 to the cutting head 20, as discussed previously.

The surgeon moves the razor sharp tip 46 of the cutting head 20 into engagement with the tissue to be removed, fragmenting the tissue. The fragmented tissue, typically a rod-like or cylindrical core, is thereafter aspirated into the external tissue collection means via the drive tube 18, suction tube 54, and vacuum hose 60. At any time during the procedure, the surgeon can adjust the amount the cutting head 20 extends out of the sheath 14 by manipulating the rotary sheath knob 33. This can be done either while the cutting head is rotating or, by releasing the trigger 22 to disconnect the motor 76 from power, when the cutting head 20 is stationary.

When the procedure is complete, the surgeon merely releases the trigger which opens the switch 81, turns off the motor 76, and precludes communication of suction to the cutting head 20. Thereafter, the rotary sheath knob 33 is returned to its initial or outwardmost position, allowing the sheath 14 to extend over and cover the cutting head 20, and the morcellator 10 is withdrawn from the port.

With reference to FIG. 5, the third embodiment of the mechanical morcellator of the present invention is shown. The third embodiment includes the handle 12, sheath 14, barrel 16, drive tube 18, cutting head 20 (FIG. 3), and trigger 22. The handle 12, which is preferably formed in two mating halves of polycarbonate or ABS plastic, provides a front aperture 24 through which the sheath 14, barrel 16, and drive tube 18 extend.

The sheath 14 has a proximal end 30 and a tapered distal end 32 (FIG. 3). The proximal end 30 of the sheath 14 is press fit into a slide switch 35 which extends upwardly through an opening in the handle 12 and is accessible for user manipulation thereof. The sheath 14, barrel 16, and drive tube 18 extend through a central opening provided by the slide switch 35. The slide switch 35 is pivotally mounted to a spring hoop 41 which, in turn, is pivotally mounted to the handle 12.

As mounted within the handle 12 to the spring hoop 41, the slide switch 35 is only capable of longitudinal movement. More specifically, the slide switch 35 is only capable of being "at rest" in either a forward position, which is illustrated in FIG. 5, or a rearward position adjacent the sheath stop 36. Preferably, movement between the forward and rearward positions is limited to about 0.435 inches. Thus, rearwardly moving the slide switch 35 longitudinally slides the sheath 14 from a first position covering the cutting head to a second position wherein the cutting head 20 extends out of the sheath. Forwardly moving the slide switch 35 returns the sheath 14 to the position covering the cutting head 20. The remaining structural features of the third embodiment are generally identical to those described previously, and will not be further described herein.

The mechanical morcellator 10 of the third embodiment operates in the following manner. Following severance of the tissue to be removed from the tissue to remain, the morcellator 10 is inserted via an existing laparoscope port. Optionally, and as discussed previously, the severed tissue may be confined or placed within an impermeable bag, preferably of nylon or the like, to prevent the migration of tissue during morcellation thereof. In the preferred embodiment the sheath 14, barrel 16, and drive tube 18 extend approximately 10.0 inches from the handle 12, allowing the cutting head 20 to reach the tissue within the patient's body. The morcellator 10 is not intended to be in operation during insertion and the electrical and mechanical means described previously prevent the unintentional operation thereof.

While the surgeon views the tissue to be removed and the distal ends 32 and 44 of the sheath 14 and cutting head 20 via a laparascope (not shown), the slide switch 35 is rearwardly moved by the surgeon from the forward position in which the sheath 14 covers the cutting head (FIG. 5) to the rearward position wherein the cutting head 20 extends out of the sheath. Thereafter, the trigger 22 and trigger latch 38 are manipulated as previously described with reference to the operation of the second embodiment to actuate the motor 76 and communicate suction to the cutting head 20. At any time during the procedure, the surgeon can cover the cutting head 20 with the sheath 14 by simply moving the slide switch 35 forwardly (i.e. toward the cutting head). This can be done either while the cutting head 20 is rotating or, by releasing the trigger 22 to disconnect the motor 76 from power, when the cutting head 20 is stationary.

When the procedure is complete, the surgeon merely releases the trigger which opens the switch 81, turns off the motor 76, and precludes communication of suction to the cutting head 20. Thereafter, the slide switch 35 is returned to its initial or forwardmost position (FIG. 5), allowing the sheath 14 to extend over and cover the cutting head 20, and the morcellator 10 is withdrawn from the port.

As should be clear from the foregoing embodiments of the present invention, the combination of the relatively moveable sheath 14, the trigger latch 38, and the switch 81 cooperate to provide a mechanical morcellator which prevents the accidental or unintentional actuation or operation thereof. Specifically, there is lost motion associated with the trigger 22 and trigger latch 38. Moreover, accidental actuation of the razor sharp tip 46 of the cutting head 20 is not possible without first rearwardly moving the trigger 22 and trigger latch 38.

While the preferred embodiments of the present invention are shown and described herein, it is to be understood that the present invention is not so limited but shall cover and include any and all modifications thereof which fall within the purview of the invention as defined by the claims appended hereto. For example, the rotary cutting head specifically described herein could be replaced by any rotary cutting device, or could be made to move longitudinally while the sheath remains stationary. Also, it should be clear that the specific dimensions included herein are merely illustrative of the relative sizes of the various components comprising the preferred embodiments presently contemplated by the inventor, and are in no way meant to limit the present invention to only the size dimensions recited herein.

What is claimed is:

1. A mechanical morcellator comprising a cutting head means, drive means operably connected to said cutting head means to rotatably drive said cutting head means, sheath means, and trigger means adapted to relatively move one of said sheath means and said cutting head means between first and second positions wherein, when in the first position, the sheath means generally surrounds the cutting head means and, when in the second position, the cutting head means extends out of the sheath means and further wherein said trigger means being engageable with the sheath means and operable to move the sheath means relative to the cutting head means, said trigger means further comprising a trigger latch, said trigger latch comprising latch means which releasably engage a latch surface on said sheath to prevent unintentional movement of said trigger, said mechanical morcellator further comprising a suction control means, said suction control means being operable to control suction force communicated to the cutting head means, and wherein the trigger means are manually operated, said suction control means and one of said sheath means and said cutting head means being responsive to movement of said trigger means between an initial position and a subsequent position so that said sheath means and cutting head means are in the first position when the trigger means is in the initial position and the sheath means and cutting head means are in the second position when the trigger means is in the subsequent position, with a one-for-one correspondence between suction force and the amount the cutting head means extends out of the sheath means between the initial and subsequent trigger positions.

2. A mechanical morcellator according to claim 1, further comprising switch means adapted to connect the drive means to power, said switch means having first and second contacts, said first contact being carried by said trigger means and being operable to engage said second contact when the trigger means is in the subsequent position.

3. A mechanical morcellator according to claim 2, wherein the trigger means comprises a sliding trigger.

4. A mechanical morcellator according to claim 1, wherein said trigger means comprises a rotary sheath knob, rotation of said sheath knob causing said sheath means to move longitudinally relative to said cutting head means.

5. A mechanical morcellator according to claim 1, wherein said trigger means comprises a slide switch, said slide switch being attached to said sheath means and being operable to longitudinally move said sheath means relative to said cutting head means.

6. A mechanical morcellator comprising a cutting head means, drive means operably connected to said cutting head means to rotatably drive said cutting head means, sheath means, and trigger means adapted to relatively move one of said sheath means and said cutting head means between first and second positions wherein, when in the first position, the sheath means generally surrounds the cutting head means and, when in the second position, the cutting head means extends out of the sheath means and further wherein said trigger means being engageable with the sheath means and operable to move the sheath means relative to the cutting head means, said trigger means further comprising a trigger latch, said trigger latch comprising latch means which releasably engage a latch surface on said sheath to prevent unintentional movement of said trigger, and further comprising a suction control means, said suction control means being operable to control suction force communicated to the cutting head means, and wherein said trigger means are manually operated and, said suction control means being responsive to movement of said trigger means between initial and subsequent positions, wherein, when the trigger means is in the initial position, a first suction force is communicated to said cutting head means and, when the trigger means is in the subsequent position, a second suction force is communicated to said cutting head means, said second suction force being greater than the first suction force.

7. A mechanical morcellator according to claim 6, wherein the drive means is responsive to movement of the trigger means between said initial and subsequent positions such that, when the trigger means is in the initial position, the drive means is in a non-operating condition and, when the trigger means is in the subsequent position, the drive means is in an operating condition.

8. A mechanical morcellator according to claim 7, wherein the trigger means comprises a trigger latch and a sliding trigger, said trigger latch comprising latch means which releasably engage a latch surface to prevent unintentional movement of said trigger.

9. A mechanical morcellator according to claim 8, wherein the sheath means moves relative to the cutting head means and the suction control means is integral with the trigger means.

10. A mechanical morcellator according to claim 9, wherein said trigger means comprises a rotary sheath knob, rotation of said sheath knob causing said sheath means to move longitudinally relative to said cutting head means.

11. A mechanical morcellator according to claim 9, wherein said trigger means comprises a slide switch, said slide switch being attached to said sheath means and being operable to longitudinally move said sheath means relative to said cutting head means.

* * * * *